United States Patent [19]
den Otter et al.

[11] 3,956,299
[45] May 11, 1976

[54] PROCESS FOR THE PREPARATION OF CYANURIC ACID

[75] Inventors: Marinus J. A. M. den Otter, Munstergeleen; Lambertus P. G. Hawinkels, Montfort; Augustinus P. H. Schouteten, Maastricht, all of Netherlands

[73] Assignee: Stamicarbon B.V., Geleen, Netherlands

[22] Filed: Apr. 24, 1975

[21] Appl. No.: 571,351

[30] Foreign Application Priority Data
Apr. 26, 1974 Netherlands...................... 7405629

[52] U.S. Cl............................ 260/248 A; 260/249.8; 260/249.5
[51] Int. Cl.$^2$.............. C07D 251/32; C07D 251/46; C07D 251/52
[58] Field of Search........... 260/248 A, 249.5, 249.8

[56] References Cited
UNITED STATES PATENTS
1,734,029    11/1929    Barsky et al.................... 260/248 X

*Primary Examiner*—John M. Ford
*Attorney, Agent, or Firm*—Cushman, Darby & Cushman

[57] ABSTRACT

An improved process for forming cyanuric acid wherein urea and/or biuret, dissolved in a solvent, are heated in the presence of a dissolved acid or a corresponding anhydride or ammonium salt to produce cyanuric acid so that byproducts ammeline and ammelide are produced in amounts no greater than 1 % by weight of the product.

13 Claims, 1 Drawing Figure

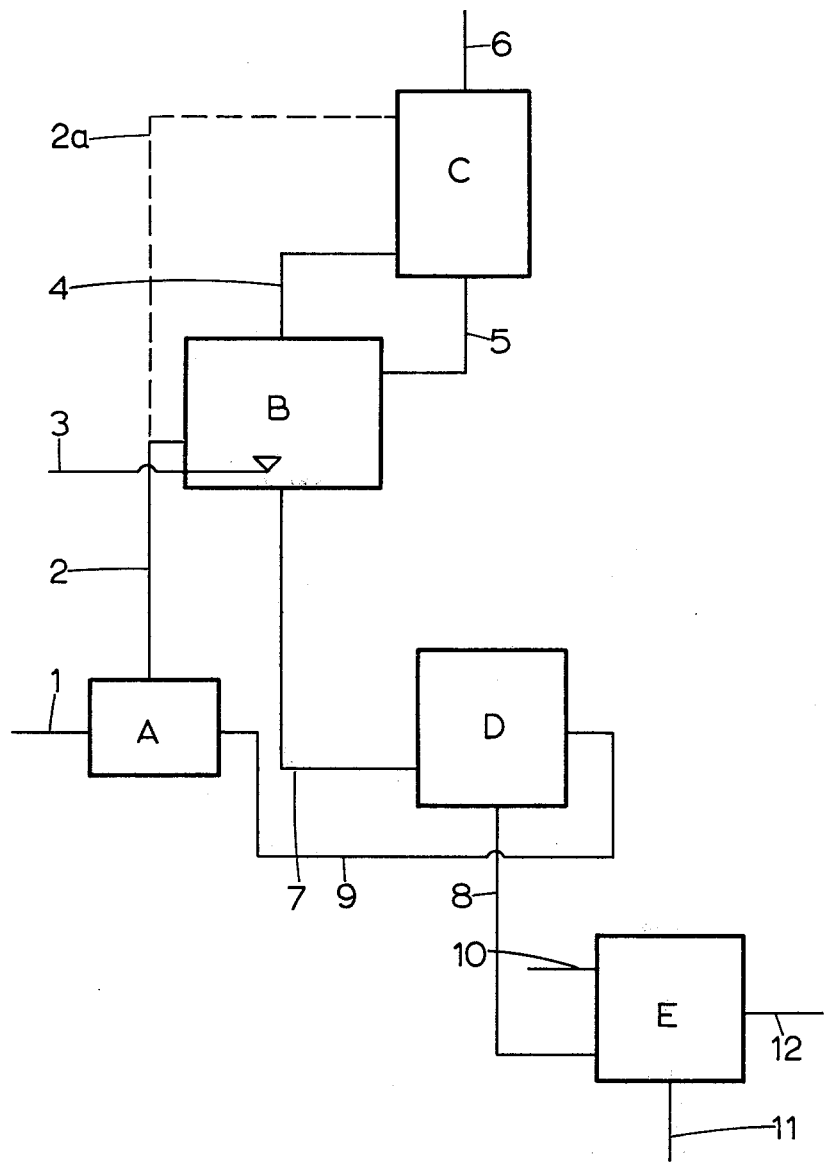

PROCESS FOR THE PREPARATION OF CYANURIC ACID

BACKGROUND OF THE INVENTION

The invention relates to a process for preparing cyanuric acid by heating a solution of urea and/or biuret in a solvent while vapor is discharged.

U.S. Pat. No. 3,563,987 discloses heating urea and/or biuret to form cyanuric acid under a subatmospheric pressure of at most 250 mm Hg and at a temperature of at least 180°C.

In the preparation of cyanuric acid by heating urea or biuret, the amount of the by-products ammelide and ammeline contained in the resulting cyanuric acid (hereinafter referred to as "ammelide content" for short) is of great importance. In general, an ammelide content of over 1 per cent by weight is commercially undesirable. It is common practice to purify crude cyanuric acid with an ammelide content of over 1% by weight by treating the crude cyanuric acid with a strongly acidic aqueous solution during which treatment ammelide and ammeline are hydrolyzed to cyanuric acid. However, such a hydrolysis step is very expensive when production of cyanuric acid is on a large scale basis so that it is important to avoid this step.

In these known processes it is possible to prepare cyanuric acid with an ammelide content of no more than 1 % by weight, but the art recognized processes impose several limitations on the choice of reaction conditions, so that the production yields of cyanuric acid are difficult to optimize.

It has been proposed in British Patent Specification 975,714 to prepare cyanuric acid by heating a dispersion of urea and an acidic catalyst in an inert diluent in which urea, cyanuric acid and the acidic catalyst are substantially insoluble. The ammelide content of the cyanuric-acid product obtained in this known process before applying a hydrolysis step is very high, about 3 % by weight, so that the hydrolysis step is inevitable for most purposes of cyanuric acid. A further draw-back of this known process is the fact that the cyanuric-acid product is contaminated with acidic catalyst which must be removed. A yet further draw-back is the substantial necessity to thoroughly mix the urea and the acidic catalyst prior to dispersion in the inert diluent. This known process can hardly be carried out as a continuous process.

SUMMARY OF THE INVENTION

According to the invention, virtually pure cyanuric acid is consequently prepared by heating a solution of urea and/or biuret in a solvent while vapor is discharged, the process being characterized in that the reaction is carried out in the presence of an acid dissolved in the reaction mixture or of an acid anhydride or ammmonium salt of a soluble acid. In this description an acid is considered as soluble if under the reaction conditions at least 0.1 % by weight, preferably at least 1 % by weight of the acid will dissolve in the reaction medium.

In the process according to the invention the ammelide content of the cyanuric-acid product is considerably reduced in comparison to the known processes.

The process according to the invention offers the advantage that the freedom of choice of reaction conditions is great and obviates the necessity of the step of hydrolysis of the by-products to purify the cyanuric acid. Thus, cyanuric acid that has exceedingly low ammelide content can be prepared without hydrolysis of crude cyanuric product to remove the by-products. Alternatively, in order to improve the economics of the process, particularly in a continuous process, it is also possible to optimize the reaction conditions (higher urea concentration, higher temperature, higher reaction rate) without the ammelide content of the cyanuric-acid product exceeding the acceptable limit of 1 % by weight without the additional and subsequent step of hydrolysis.

The process according to the invention is particularly suitable for continuous processes.

DETAILED DESCRIPTION OF THE INVENTION

As set forth above the process of the invention is directed to heating urea and/or biuret dissolved in the reaction medium containing a dissolved acid or a corresponding anhydride or ammonium salt to produce cyanuric acid, vapor being discharged during the reaction.

In the process according to the invention use is made of a solvent in which the urea and/or biuret is/are relatively soluble, but in which the cyanuric acid is relatively insoluble. The solvent must have sufficient thermal stability, under the reaction conditions must preferably be chemically inert, and must have a sufficiently high boiling point. Suitable solvents are e.g. dialkyl-sulphones or cyclic sulphones with at most 12 carbon, halogen-substituted cresols and phenols, N-substituted urethanes and cyclic urethanes with phenyl or alkyl groups of at most 6 carbon atoms as substituents. Examples of suitable solvents are dimethyl sulphone, dipropyl sulphone, sulpholane, chlorocresols, and 5-methyl-2-oxazolidinone. Sulpholane or a derivative of it substituted with one or more methyl groups are particularly suitable.

During the reaction, vapour is discharged from the reaction vessel. Particularly good results are obtained if the vapor is discharged by stripping with a stripping gas. Examples of suitable stripping gases are nitrogen and carbon dioxide. Particularly good results are also obtained if the reaction is carried out under boiling conditions.

The acid or acid anhydride or ammonium salt, used in accordance with the invention is preferably an acid in accordance respectively corresponds to an acid that is at least fairly soluble in the reaction medium and which is not volatile under the reaction conditions. The latter fact implies that, at the reaction pressure, the boiling point of the acid must preferably be higher than the reaction temperature. Moreover, the acid must have sufficient thermal stability. Suitable acids, anhydrides and ammonium salts are, in particular, organic acids and anhydrides and ammonium salts thereof, such as, e.g., high-boiling, preferably but not necessarily saturated aliphatic carboxylic acids with, preferably, at most 24 carbon atoms, or the corresponding anhydrides or ammonium salts; aromatic (aryl, alkaryl or aralkyl) carboxylic acids with, preferably, at most 12 carbon atoms, and the corresponding anhydrides or ammonium salts; aliphatic or aromatic (aryl, alkaryl or aralkyl) dicarboxylic acids with, preferably, at most 12 carbon atoms, and the corresponding anhydrides or mono- or diammonium salts; or similar polycarboxylic acids of up to 12 carbon atoms or the anhydrides or mono-, di-, or polyammonium salts of these acids. Examples are palmitic acid, oleic acid, stearic acid, benzoic acid, toluenecarboxylic acids, naphthoic acids, phenylacetic acid, succinic acid, phthalic acid, and 1,3,5-pentanetricarboxylic acid, and the corresponding anhydrides and ammonium salts. The acids and the corresponding anhydrides or ammonium salts can be unsubstituted or substituted and may have substituents that are inert under the reaction conditions, such as alkyl groups with, e.g., 1–4 carbon atoms, aryl groups with, e.g., at most 8 carbon atoms, or halogen substituents. A particularly suitable acid is benzoic acid, which is readily available.

The concentration of the acid or the anhydride or ammonium salt thereof used in the reaction medium may vary within wide limits. The influence is clearly noticeable at such low concentrations as, e.g. 0.1 % by weight, calculated to the total weight of the reaction mixture. The use of an acid concentration of over 150 grams per liter is possible, but offers no advantage. The acid concentration preferably ranges between 10 to 150 grams per liter.

The reaction temperature usually ranges between 150 and 280°C, preferably between 170° to 220°C, and is preferably lower than 200°C if the solvent used is sulpholane or a derivative of it substituted with one or more methyl groups. At higher temperatures, the reaction proceeds faster, but the chance of increasing ammelide as a by-product and of solvent being decomposed increases.

The reaction pressure is not directly critical and may vary, for instance, between 0.01 and 10 atmospheres. Preferably the process is carried out at a pressure up to 1 atmosphere. If the reaction temperature is at least of the boiling point of the reaction mixture, the pressure will usually have to be lower than 1 atmosphere. Use is preferably made of a pressure between 0.01 and 0.25 atmosphere.

Preferably, the concentration of starting urea and/or biuret in the reaction mixture is not too high, as the ammelide content of the cyanuric-acid product will then increase. Concentrations of below 600 grams per liter are very suitable, but higher urea and/or biuret concentrations may be used. The use of a concentration of over the saturation concentration does not offer any advantage.

At very low concentrations a good product is obtained, but the cost per unit product is high. Preferably the starting concentration of urea and biuret ranges between 200 and 400 grams per liter.

The process according to the invention may be carried out batchwise, but is also very suitable for being realized as a continuous process.

DESCRIPTION OF THE DRAWINGS

One possible realization of a continuous process according to the invention is shown diagrammatically in the drawing annexed.

1 is a conduit-inlet means communicating with a dissolving vessel A. 2 is a conduit means between A and reaction vessel B allowing the contents of A to flow to B. 3 is a means for introducing stripping gas into B. 4 is a vapor escape means, 4 being in communication with condenser C. 5 is a conduit between C and B, 5 providing means for returning condensed solvent from C to B. 6 which is in communication with condenser C is a discharge means for allowing escape of non-condensed gases. D is a separator which is in communication with B via conduit 7. 8 is a conduit means between D and washing installation E. 10 is a conduit-inlet means to E for allowing introduction of wash liquor into E. 11 is a discharge means in communication with E allowing discharge of used wash liquor, while 12 is a discharge means for products purified in E.

Urea and/or biuret are fed through a conduit 1 to a dissolving vessel A, in which the starting material(s) is (are) dissolved in the solvent used, sulpholane in this case. The solution flows by way of 2 to reaction vessel B, where the conversion into cyanuric acid is effected. If so desired, a stripping gas, e.g. nitrogen, may be fed to B through 3. A gas mixture consisting of sulpholane vapor, ammonia and stripping gas, if used, escapes through 4 and is fed to condenser C. Condensed solvent flows back to B through 5. Condenser C may be embodied as a scrubber, the scrubbing liquid being preferably a solution of urea and/or biuret in the solvent used, which is fed in through conduit means 2a. Non-condensed gas escapes from C by way of 6. This gas consists of virtually pure ammonia or a mixture of ammonia and stripping gas from which ammonia can easily be recovered.

A suspension of cyanuric acid in the solvent flows from reactor B through 7 to separator D. Here the cyanuric acid is separated by filtration, precipitation, decantation, centrifugation, or in any other suitable manner known in the art. The solid product is passed through 8 to a washing installation E, where the product is washed with washing liquor supplied through 10. The washing liquor used can be water, which leaves the washing installation through 11. Pure cyanuric acid is discharged through 12. Optionally, the cyanuric acid product leaving D through 8 can be subjected to acid hydrolysis, e.g. with nitric acid, in a known manner to hydrolyze the by-products ammelide and ammeline to cyanuric acid. Normally the hydrolysis step is not necessary, however, as the ammelide content of the cyanuric acid process is already sufficiently low for most applications. The mother liquor separated off in D, which often still contains unconverted urea and/or biuret and is saturated with cyanuric acid, flows back to dissolving vessel A through 9.

At the start of the continuous process a given amount of solvent and a given amount of the acid used, e.g. benzoic acid, are put in B. Solvent and acid remain in circulation; losses, if any, may be made up through conduits (not shown) somewhere in the cycle, preferably at A.

The invention will be elucidated with reference to the following examples and comparative experiments.

EXAMPLES AND COMPARATIVE EXPERIMENTS

In each of the examples and comparative experiments mentioned in the Table, the amount of sulpholane mentioned in column 2, which may or may not contain benzoic acid or ammonium benzoate (column 4), is heated to about 160°C with stirring. Subsequently, the amount of urea stated is fed to the reactor and the contents are heated further to the reaction temperature indicated. When this temperature is reached, the pressure is lowered, or nitrogen is passed into the liquid, as indicated in the Table.

The start of the reaction time is taken to be the moment at which the desired temperature and pressure are reached, or the introduction of nitrogen is started.

After the reaction time has elapsed, the pressure is reduced to atmospheric (or the nitrogen feed is stopped), and the resulting suspension is cooled to 30°C. After filtration the cake is washed with benzene and dried.

The Table shows the amounts of cyanuric acid and ammelide (including ammeline), of the resulting solid substance (columns 8 and 9). The solid substance comprises cyanuric acid, ammelide, ammeline and unconverted urea and biuret which have also crystallized. If filtration is effected at high temperature, urea and biuret remain in solution, so that the resulting cyanuric acid product contains only traces of other impurities in addition to ammelide and ammeline. The contents of cyanuric acid and ammelide of the product that would be obtained if hot filtration is used were calculated from the contents given in columns 8 and 9 and are given in columns 10 and 11. In example VII the suspension is filtered at 150°C instead of 30°C; in this case the content in column 11 is directly measured and the content in column 10 is calculated therefrom.

Cyanuric acid is useful e.g. as starting material for the production of well-known desinfecting and bleaching agents such as dichlorocyanuric acid and trichlorocyanuric acid and of other well-known useful chemicals such as tris(2-hydroxyethyl)isocyanurate and triallyl-isocyanurate which may be used as comonomers or additives in a great range of well-known polymers.

an aliphatic or aryl-, alkaryl- or aralkyldicarboxylic acid of up to 12 carbon atoms or a corresponding anhydride or mono- or diammonium salt; or polycarboxylic acids of up to 12 carbon atoms or a corresponding anhydride or mono-, di- or poly-ammonium salt.

3. The process according to claim 1, wherein the reaction is undertaken in the presence of a carboxylic acid dissolved in the reaction mixture, said carboxylic acid containing up to 24 carbon atoms and present in an amount of at least 0.1 % by weight of the reaction mixture.

4. The process of claim 3, wherein said acid is benzoic acid.

5. The process according to claim 1, wherein the reaction is undertaken in the presence of an ammonium salt of a soluble carboxylic acid, said carboxylic acid containing up to 24 carbon atoms, said ammonium salt being present in an amount of at least 0.1 % by weight of the reaction mixture.

6. The process of claim 5, wherein said ammonium salt is ammonium benzoate.

7. The process of claim 1, wherein said acid or anhydride or ammonium salt thereof is present in the reaction mixture in a concentration of between 10 and 150 grams per liter.

| column 1 example | 2 sulpholane ml | 3 urea g | 4 benzoic acid g | 5 pressure (atm) | 6 temp. °C | 7 time h | 8 9 composition of solid substance cold filtration | | 10 11 hot filtration | |
|---|---|---|---|---|---|---|---|---|---|---|
| | | | | | | | cyanuric acid % by w. | ammelide % by w. | cyanuric acid % by w. | ammelide % by w. |
| I | 300 | 100 | 25 | about 0.05 [1] | 185 | 1 | 91.4 | 0.1 | 99.9 | 0.1 |
| II | 300 | 100 | 25 | 1 at/N$_2$ [2] | 185 | 1 | 98.5 | 0.2 | 99.8 | 0.2 |
| III | 100 | 60 | 15 | about 0.05 [1] | 185 | 1 | 66.6 | 0.7 | 99.0 | 1.0 |
| comparative experiment A | 100 | 60 | 0 | about 0.05 [1] | 185 | 1 | 73.9 | 2.3 | 97.0 | 3.0 |
| IV | 100 | 60 | 15 | about 0.05 [1] | 190 | 2 | 99.5 | 1.0 | 99.0 | 1.0 |
| V | 100 | 60 | 15 | about 0.15 [1] | 200 | 1 | 95.4 | 1.4 | 98.6 | 1.4 |
| VI | 300 | 180 | 4.5 | about 0.05 [1] | 185 | 1 | 84.0 | 1.3 | 98.5 | 1.5 |
| VII | 200 | 70 | 20 [4] | about 0.05 [1] | 185 | 1 | — | — | 99.6 | 0.4 |
| comparative experiment B | 300 | 180 | 4.5 | about 0.15 [3] | 185 | 1 | 39.3 | 1.5 | 96.3 | 3.7 |

[1] boiling reaction mixture
[2] nitrogen passed through at atmospheric pressure
[3] non-boiling reaction mixture
[4] ammonium benzoate instead of benzoic acid

What is claimed is:

1. In a process for preparing cyanuric acid with low content of the by-products ammelide and ammeline by heating a solution of urea, biuret or mixtures thereof in a solvent while vapor is discharged, the improvement comprising undertaking the reaction in the presence of a carboxylic acid dissolved in the reaction mixture or of an anhydride or ammonium salt of a soluble carboxylic acid, said carboxylic acid containing up to 24 carbon atoms and present in an amount of at least 0.1 % by weight of the reaction mixture.

2. The process according to claim 1, wherein said carboxylic acid has a boiling point that is higher than the reaction temperature used, said carboxylic acid or anhydride or ammonium salt thereof being a saturated aliphatic carboxylic acid of up to 24 carbon atoms or a corresponding anhydride or ammonium salt; an aryl-, alkaryl- or alkarylcarboxylic acid of up to 12 carbon atoms or a corresponding anhydride or ammonium salt;

8. The process of claim 1, wherein said vapor is stripped from the reaction mixture by passing a stripping gas through the reaction mixture.

9. The process of claim 1, wherein the reaction is undertaken at the boiling temperature of the reaction medium.

10. The process of claim 1, wherein the solvent used is sulpholane or a derivative of it substituted with one or more methyl groups.

11. The process of claim 10, wherein a reaction temperature of between 170° and 200°C is employed.

12. The process of claim 1, wherein the reaction pressure used ranges between 0.01 and 0.25 atmosphere.

13. The process of claim 1, wherein the starting concentration of urea, biuret or mixtures thereof ranges between 200 and 400 grams per liter.

* * * * *